US011532399B2

(12) United States Patent
Park et al.

(10) Patent No.: US 11,532,399 B2
(45) Date of Patent: Dec. 20, 2022

(54) IDENTIFYING HIGH TISSUE DENSITY IN IMAGES USING MACHINE LEARNING

(71) Applicant: International Business Machines Corporation, Armonk, NY (US)

(72) Inventors: Sun Young Park, San Diego, CA (US); Dustin M. Sargent, San Diego, CA (US)

(73) Assignee: Merative US L.P., Ann Arbor, MI (US)

(*) Notice: Subject to any disclaimer, the term of this patent is extended or adjusted under 35 U.S.C. 154(b) by 188 days.

(21) Appl. No.: 16/653,466

(22) Filed: Oct. 15, 2019

(65) Prior Publication Data

US 2021/0110930 A1 Apr. 15, 2021

(51) Int. Cl.
*G16H 50/30* (2018.01)
*G16H 30/40* (2018.01)
*G06N 3/08* (2006.01)
*G06N 3/04* (2006.01)

(52) U.S. Cl.
CPC ............... *G16H 50/30* (2018.01); *G06N 3/04* (2013.01); *G06N 3/08* (2013.01); *G16H 30/40* (2018.01)

(58) Field of Classification Search
CPC ........ G16H 50/30; G16H 30/40; G16H 50/20; G06N 3/08; G06N 3/04
See application file for complete search history.

(56) References Cited

U.S. PATENT DOCUMENTS 7,903,861 B2 * 3/2011 Luo .......................... G06T 7/12 382/132
9,058,650 B2 * 6/2015 El-Hilo .................. G06T 7/136
9,519,966 B2 12/2016 Ghouti et al.
9,895,121 B2 2/2018 Abdolell et al.
2016/0314579 A1 * 10/2016 Ghouti ................. G06V 10/255
2019/0005684 A1 * 1/2019 De Fauw ............ G06K 9/6292

(Continued)

FOREIGN PATENT DOCUMENTS

WO WO-2019084697 A1 * 5/2019 .......... G06K 9/3233

OTHER PUBLICATIONS

S. Park et al., "Breast density follow-up decision support system using deep convolutional models," Proc. SPIE 10950, Medical Imaging 2019: Computer-Aided Diagnosis, 109500G (Mar. 13, 2019); https://doi:org/10.1117/12.2513047, 10 pages (Grace Period Disclosure under 35 U.S.C. 102(b)(1)(A)).

(Continued)

*Primary Examiner* — Robert A Sorey
*Assistant Examiner* — Kimberly A. Sass
(74) *Attorney, Agent, or Firm* — Edell, Shapiro & Finnan, LLC

(57) ABSTRACT

Methods and systems and computer readable media are provided for processing digitized radiology images of a patient's tissue to perform a tissue density assessment. A set of radiology images is analyzed with a tissue density image classifier, wherein the tissue density classifier includes a plurality of classifiers. A features vector is generated, for each processed image in the set of radiology images, based on the processing. The features vector is provided, for each processed image in the set of radiology images, to a tissue density classifier to obtain an output. A final tissue density score is assigned based on the output of the tissue density classifier.

20 Claims, 9 Drawing Sheets

410
UNSUPERVISED PATCH MODEL
545
CNN RISK CLASSIFIER
ASSIGN IMAGE INTO A BOUNDARY DECISION CATEGORY (CATEGORY B OR C)
420
310-1
510
540
PATCH MODEL AND RISK CLASSIFIER
115

(56) References Cited

U.S. PATENT DOCUMENTS

2020/0074632 A1* 3/2020 Heindl .................. A61B 6/502

OTHER PUBLICATIONS

J. Xu et al., "Classifying Mammographic Breast Density by Residual Learning." (Submitted on Sep. 21, 2018), https://arxiv.org/abs/1809.10241, 11 pages.
N. Wu, "Breast density classification with deep convolutional neural networks." (Submitted on Nov. 10, 2017), https://arxiv.org/abs/1711.03674, 5 pages.
K. Bovis and S. Singh, "Classification of Mammographic Breast Density Using a Combined Classifier Paradigm." In Proceedings of the 4th International Workshop on Digital Mammography, Nijmegen, Netherlands, Jun. 7-10, 2002; pp. 177-180, 4 pages.
N. Kaiser et al., "Mammographic breast density classification using a deep neural network: assessment based on inter-observer variability," Proc. SPIE 10952, Medical Imaging 2019: Image Perception, Observer Performance, and Technology Assessment, 109520O (Mar. 4, 2019); https://doi.org/10.1117/12.2513420, 7 pages.
A. Mohamed, et al., "A deep learning method for classifying mammographic breast density categories," Medical Physics, Jan. 2018; 45(1):314-21, 8 pages (available online, Dec. 22, 2017, https://aapm.onlinelibrary.wiley.com/doi/epdf/10.1002/mp.12683).
P. Fonseca et al., "Breast Density Classification with Convolutional Neural Networks." In: C. Beltrán-Castañón (ed)., Progress in Pattern Recognition, Image Analysis, Computer Vision, and Applications. CIARP 2016. Lecture Notes in Computer Science, vol. 10125. Springer, Cham pp. 101-108, 2017, 8 pages.

* cited by examiner

IDENTIFYING HIGH TISSUE DENSITY IN IMAGES USING MACHINE LEARNING

The following disclosure is submitted under 35 U.S.C. § 102 (b)(1)(A): "Breast density follow-up decision support system using deep convolutional models," Park et al., made available to the public on Mar. 13, 2019 as published in Proc. SPIE 10950, Medical Imaging 2019: Computer-Aided Diagnosis, 10 pages.

BACKGROUND

1. Technical Field

Present invention embodiments relate to machine learning systems for image processing, and in particular, to utilize deep learning techniques to identify individuals for further medical imaging studies based on tissue density classification.

2. Discussion of the Related Art

Medical guidelines for recommending follow-up screening for breast cancer are based, at least in part, on breast tissue density assessment. In particular, high density tissue regions may mask cancerous lesions or masses on mammograms leading to false negative results.

Previous medical standards (e.g., Breast Imaging Reporting and Data System (BIRADS) $4^{th}$ edition) have assessed risk based on four breast tissue density classes relying on visual assessment by a physician or other medical personnel of the percentage of fibroglandular tissue. These classes include: class 1 (0-25%), class 2 (25-50%), class 3 (50-75%), and class 4 (75-100%). More recent medical guidelines (e.g., BIRADS $5^{th}$ edition) have eliminated these percentages and have replaced visual assessment with a more subjective analysis. These classes of the more recent $5^{th}$ edition guidelines include: class A (almost entirely fatty tissue), class B (scattered areas of fibroglandular tissue density), class C (heterogeneously dense tissue), and class D (extremely dense tissue). For patients classified into class C or D, additional screening with a different modality (e.g., MRI) is frequently recommended.

Because the evaluation criteria and class descriptions are highly subjective, there is high variability in breast tissue density assessment. Further, changing standards have led to inconsistencies in categorization, since the same image may be classified differently based on different standards (e.g., legacy standards versus current standards). For example, a patient's mammography image may be classified differently under the current standards as compared to legacy standards even though the images are the same.

Although categorization is subjective, not all classification errors carry the same weight. For example, and based on $5^{th}$ edition BIRADS guidelines, a class A image that is classified as a class B image or a class D image that is classified as a class C image does not typically lead to a change in patient care. However, the boundary between class B (scattered density) and class C (heterogeneous density), which forms the boundary for decision making for follow-up screening, impacts patient care, as an individual classified as class B will not be recommended for follow-up screening while an individual classified as class C typically will be recommended for follow up screening. Further, not only is visual assessment subjective, but changing medical guidelines also may lead to significant variability in breast tissue density classification, which leads to inconsistent treatment of patients whose images are classified into classes along decision boundaries.

SUMMARY

According to embodiments of the present invention, methods, systems, and computer readable media are provided for processing digitized radiology images of a patient's tissue to perform a tissue density assessment. A set of radiology images of a patient's tissue is analyzed with a tissue density classifier, wherein the tissue density classifier includes a plurality of classifiers. A features vector is generated, for each processed image in the set of radiology images, based on the processing. The features vector is provided, for each processed image in the set of radiology images, to a tissue density classifier to obtain an output. A final tissue density score is assigned based on the output of the tissue density classifier.

These techniques may be used to classify breast tissue density into different classes in a reliable and consistent manner. Further, identification of candidates for follow-up testing, which relies upon classification into classes along a treatment decision boundary, may be performed in a reliable and consistent manner. Patients classified into a class indicative of high density (e.g., class C) may be recommended for follow-up testing using a different modality, e.g., such as MRI.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

DETAILED DESCRIPTION

Methods, systems, and computer readable media are provided for assessing tissue density based on novel machine learning techniques that achieve accurate and objective tissue density classification. In some aspects, the tissue density image classifier is based on two models: a normal four class tissue density classification (W, X, Y, Z) and a two class low (class W or class X) vs. high (class Y or class Z) tissue density classification. In other aspects, the tissue density image classifier is based on three models: a normal four class tissue density classification (W, X, Y, Z), a two class low (class W or class X) vs. high (class Y or class Z) tissue density classification, and a refinement classification improving the accuracy of a boundary decision classifier (between class X and class Y), wherein the boundary decision classifier determines whether further testing is recommended. In some cases, classes W, X, Y, Z, may correspond to classes A, B, C, D, of the $5^{th}$ edition BIRADS guidelines. In other cases, the classes may refer to other standards.

Figure 1:
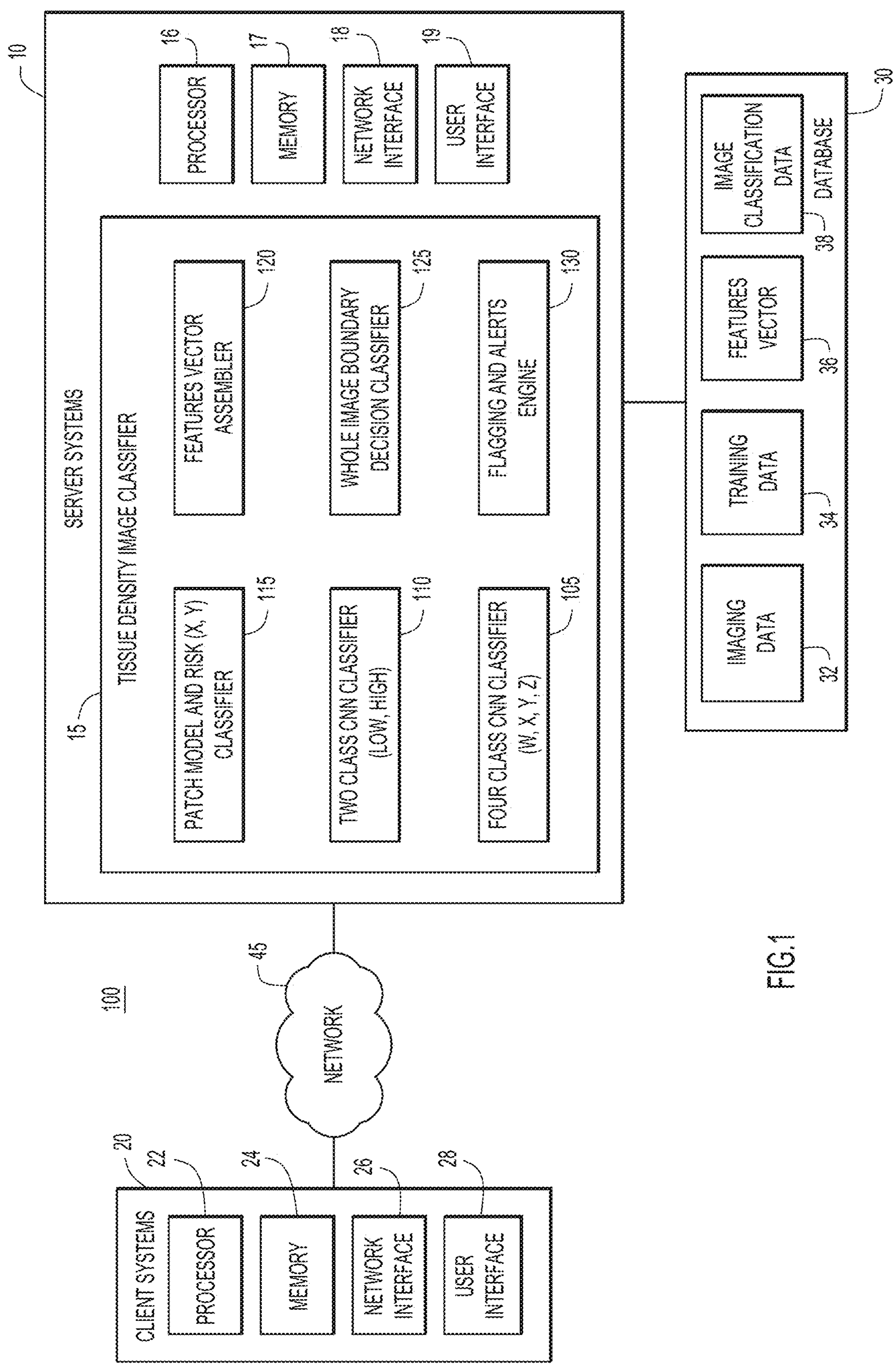
FIG. 1 is a diagrammatic illustration of an example computing environment for the tissue density image classifier according to an embodiment of the present invention.

An example environment for use with present invention embodiments is illustrated in FIG. 1. Specifically, the environment includes one or more server systems 10, one or more client or end-user systems 20, a database 30, and network 45. Server systems 10 and client systems 20 may be remote from each other and may communicate over a network 45. The network may be implemented by any number of any suitable communications media, such as a wide area network (WAN), a local area network (LAN), Internet, Intranet, etc. Alternatively, server systems 10 and client systems 20 may be local to each other, and may communicate via any appropriate local communication medium, such as local area network (LAN), hardwire, wireless link, Intranet, etc.

Client systems 20 enable users to submit datasets to server systems 10 for training a tissue density image classifier 15 and for using this system to identify patients at high risk of obtaining inaccurate imaging results, e.g., from mammography, due to high tissue density. The server systems 10 include a tissue density image classifier 15 comprising one or more of a four class convolutional neural network (CNN) classifier 105, a two class CNN classifier 110, a patch model and risk classifier 115, a features vector assembler 120, a whole image boundary decision classifier 125, and a flagging and alerts engine 130, as described herein.

A database 30 may store various information for the analysis, such as imaging data 32, training data 34, features vector 36, and image classification data 38, etc. The imaging data 32 contains mammography or other types of imaging data files whose analysis may be affected by tissue density. Training data 34 may contain training data to train the various classifiers in the system. Each classifier may have a corresponding training dataset to train the respective classifier (e.g., a training dataset may be provided for the four class CNN classifier, another training dataset may be provided for the two class CNN classifier, still other training datasets may be provided for the patch model classifier and for the risk classifier, and another training dataset may be provided for the whole image boundary decision classifier). Once trained, the tissue density image classifier 15 may be used to identify patients who are at risk of inaccurate mammography results due to high tissue density. In some aspects, the training datasets may be weakly labeled (such that the image as a whole is labeled, for example, as containing high density or low density tissue or as having lesions or masses), but boundaries showing where on the image that the regions of high density or masses are located are not provided.

Features vector 36 contain probability outputs from one or more of the four class classifier 105, the two state classifier 110 and the patch model and risk classifier 115. The probability outputs may be stored in vector format, e.g., along with a weighting factor, and provided to the whole image boundary decision classifier 125 for further analysis.

Image classification data 38 contains the output of the whole image boundary decision classifier 125, which classifies images into class W, class X, class Y or class Z. In some cases, classes X and Y may lie on a decision boundary such that if the image is classified into class X, no further follow-up testing is recommended, and if the image is classified into class Y, then further follow-up testing is recommended.

The database system 30 may be implemented by any conventional or other database or storage unit, may be local to or remote from server systems 10 and client systems 20 and may communicate via any appropriate communication medium, such as local area network (LAN), wide area network (WAN), Internet, hardwire, wireless link, Intranet, etc. The client systems may present a graphical user interface, such as a GUI, etc., or other interface, such as command line prompts, menu screens, etc., to solicit information from users pertaining to the desired datasets, patient health information, and may provide reports including analysis results of the imaging data, including identifying patients at risk for inaccurate or obscured imaging analysis due to high density tissue as well as follow-up testing, e.g., using a different modality.

Server systems 10 and client systems 20 may be implemented by any conventional or other computer systems preferably equipped with a display or monitor, a base (including at least one hardware processor (e.g., microprocessor, controller, central processing unit (CPU), etc.), one or more memories and/or internal or external network interfaces or communications devices (e.g., modem, network cards, etc.), optional input devices (e.g., a keyboard, mouse or other input device), and any commercially available and custom software (e.g., server/communications software, tissue density image classification software 15, browser/interface software, etc.). By way of example, the server/client includes at least one processor 16, 22 one or more memories 17, 24 and/or internal or external network interfaces or communications devices 18, 26 such as a modem or network cards, and a user interface 19, 28 etc. The optional input devices may include a keyboard, mouse, or other input device.

Alternatively, one or more client systems 20 may perform tissue density image classification as a stand-alone unit. In a stand-alone mode of operation, the client system stores or has access to the data, such as imaging data 32, training data 34 and may generate features vector 36 and image classification data 38. The stand-alone unit includes tissue density image classifier 15. The graphical user or other interface 19, 28, such as a GUI, command line prompts, menu screens, etc., solicits information from a corresponding user pertaining to the desired imaging data, and may provide reports including analysis results including identifying patients at risk for inaccurate or obscured imaging analysis due to high density tissue and recommendations for follow-up testing, e.g., using a different modality.

Tissue density image classifier 15 may include one or more modules or units to perform the various functions of present invention embodiments described herein. The various modules, four class CNN classifier 105, two class classifier 110, patch model and risk classifier 115, features vector assembler 120, whole image boundary decision classifier 125, and flagging and alerts engine 130, etc., may be implemented by any combination of any quantity of software and/or hardware modules or units, and may reside within memory 17 of the server for execution by processor 16. These modules are described in additional detail below.

Four class CNN classifier 105 may be configured to classify an image into one of four classes. The four class CNN classifier produces four probabilities ($P_W$, $P_X$, $P_Y$, $P_Z$) per image, which corresponds to a likelihood of being classified into a particular class of tissue density. These probabilities may correspond to BIRADS $5^{th}$ edition annotations such as classes A, B, C, D, or any other classification. For example, based on $5^{th}$ edition BIRADS guidelines, class A may be defined as "almost entirely fatty," class B may be defined as "scattered areas of fibroglandular density," class C may be defined as "heterogeneously dense," and class D may be defined as "extremely dense." These results may be provided to the features vector assembler for aggregation into a features vector.

Two class CNN classifier 110 may be configured to classify an image into one of two classes. The two class CNN classifier produces two probabilities ($P_{low}$, $P_{high}$) per image, which corresponds to a likelihood of being classified into a low tissue density class or a high tissue density class. For example, the low class may include classes W and X, as defined previously, while the high class may include classes Y and Z, as defined previously. These results may be provided to the features vector assembler for aggregation into a features vector. These probabilities may correspond to BIRADS 5th edition guidelines such that the low class includes classes A and B and the high class includes classes C and D.

Patch model and risk classifier 115 may be configured to classify an image into one of two classes. This classifier produces two probabilities ($P_{X2}$, $P_{Y2}$) per image, which corresponds to a likelihood of being classified into class X or class Y. When mapped to BIRADS standards, class X corresponds to class B and is defined as "scattered areas of fibroglandular density" and class Y corresponds to class C and is defined as "heterogeneously dense." These classes represent the boundary at which a decision is made for recommending further testing in a different modality. These results may be provided to the features vector assembler for aggregation into the features vector.

The whole image boundary decision classifier 125 may accept a features vector as input and may analyze the features vector along with corresponding weighting values for the probabilities using a classifier (e.g., an ensemble classifier such as a random forest classifier) to arrive at an overall result for the image analysis. The output assigns an image into one of the four respective classes, based on the output of the four class classifier, two class classifier and patch model and risk classifier 115. In some cases, the features vector may contain six probabilities ($P_{low}$, $N_{high}$, $P_W$, $P_X$, $P_Y$, $P_Z$) per image, which for four images, corresponds to a total of 24 features. In other cases, the features vector may contain eight probabilities ($P_{low}$, $P_{high}$, $P_W$, $P_X$, $P_Y$, $P_Z$, $P_{X2}$, $P_{Y2}$) per image, which for four images, corresponds to a total of 32 features. Classes may be established based on a BIRADS classification system, which lists various classes of tissue.

Flagging and alerts engine 130 may send out notification to physicians or other health care professionals, when a patient is classified into class Y or Z, both high density categories, to ensure timely follow-up.

Figure 2:
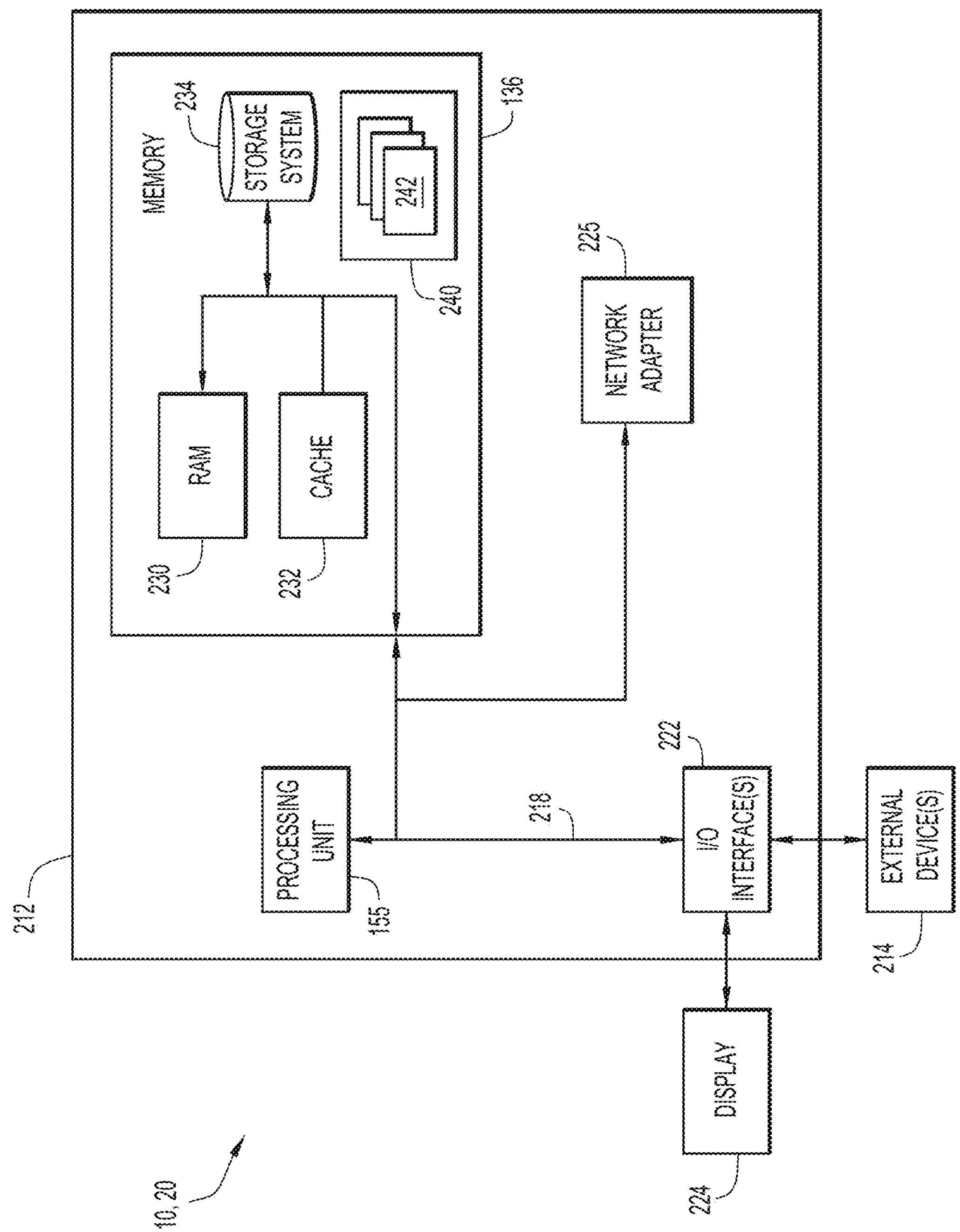
FIG. 2 is an example computing device for the computing environment of FIG. 1, according to an embodiment of the present invention.

Client systems 20 and server systems 10 may be implemented by any suitable computing device, such as computing device 212 shown in FIG. 2 for computing environment 100. This example is not intended to suggest any limitation as to the scope of use or functionality of embodiments of the invention described herein. Regardless, computing device 212 is capable of being implemented and/or performing any of the functionality set forth herein.

In the computing device, there is a computer system which is operational with numerous other general purpose or special purpose computing system environments or configurations. Examples of well-known computing systems, environments, and/or configurations that may be suitable for use with the computer system include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules (e.g., tissue density image classifier 15 and its corresponding modules), being executed by a computer system. Generally, program modules may include routines, programs, objects, components, logic, data structures, and so on that perform particular tasks or implement particular abstract data types.

Computer system 212 is shown in the form of a general-purpose computing device. The components of computer system 212 may include, but are not limited to, one or more processors or processing units 155, a system memory 136, and a bus 218 that couples various system components including system memory 136 to processor 155.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and it includes both volatile and non-volatile media, removable and non-removable media.

System memory 136 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 136 may include at least one program product having a set (e.g., at least one) of program modules that are configured to carry out the functions of embodiments of the invention.

Program/utility 240, having a set (at least one) of program modules 242 (e.g., tissue density image classifier 15 and its corresponding modules, etc.) may be stored in memory 136 by way of example, and not limitation, as well as an operating system, one or more application programs, other program modules, and program data. Each of the operating system, one or more application programs, other program modules, and program data or some combination thereof, may include an implementation of a networking environment. Program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 225. As depicted, network adapter 225 communicates with the other components of computer system 212 via bus 218. It should be understood that although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 3:
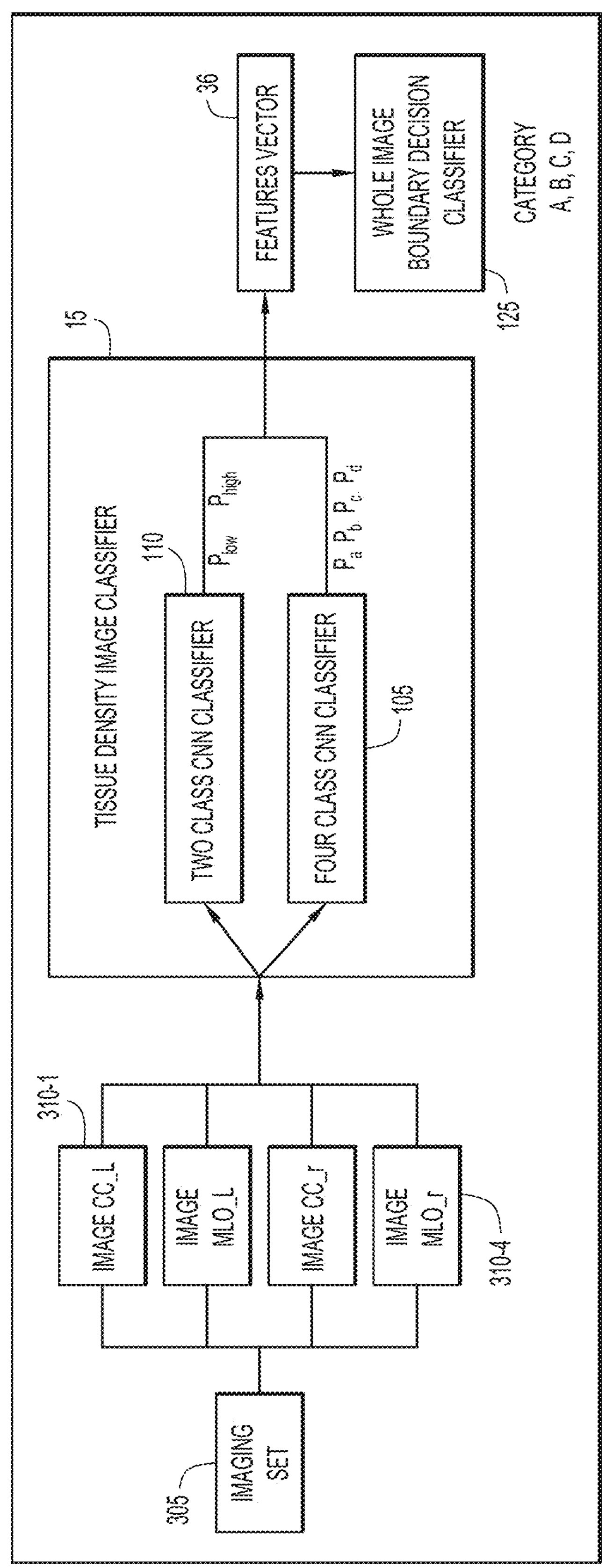
FIG. 3 is a flow diagram showing example data components for a first classifier, according to an embodiment of the present invention.
Figure 4:
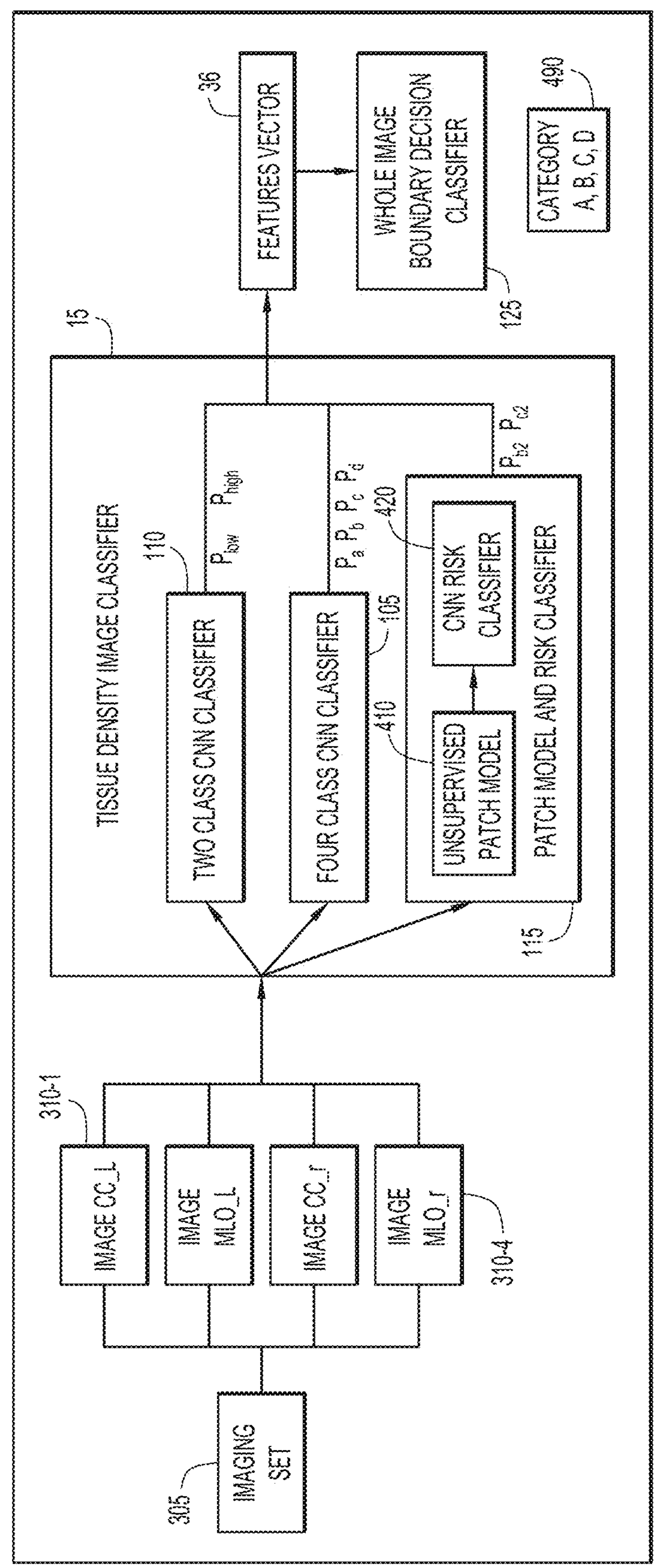
FIG. 4 is a flow diagram showing example data components for a second classifier including a patch model and risk classifier, according to an embodiment of the present invention.

Two different models for tissue classification are provided. The first classifier uses a four class and a two class classifier as shown in FIG. 3. The second model uses a four class classifier, a two class classifier, and a patch model and risk classifier as shown in FIG. 4. The first model may be used as part of an automated reporting system, and the second model may be used to make follow-up screening recommendations.

FIG. 3 shows a flow diagram for components of a two model tissue density classifier, according to the embodiments provided herein. In this embodiment, two convolutional neural networks CNNs are trained for breast tissue density classification. Both the two class CNN classifier and the four class CNN classifier may utilize deep learning models trained on weakly labeled images to classify images, e.g., based on BIRADS breast composition classes A-D.

In this example, a set of imaging data 305, comprising four mammogram images 310-1 to 310-4, are provided to the tissue density image classifier 115, and in particular, to the four class CNN classifier 105 and the two class CNN classifier 110. The four standard images 310-1 to 310-4 include different views, e.g., craniocaudal left, craniocaudal right, mediolateral oblique left, and mediolateral oblique right. Each image may be analyzed to provide six probabilities per image, for a total of 24 features for the imaging set.

The four class CNN classifier 105 produces four probabilities ($P_W$, $P_X$, $P_Y$, $P_Z$) per image, based on four tissue densities (W, X, Y, Z). In this case, these classes map to a BIRADS 5$^{th}$ edition standard (class A, class B, class C, class D), which corresponds to a likelihood of being classified into a particular BIRADS class. As previously discussed, BIRADS 5$^{th}$ edition class A is defined as "almost entirely fatty," class B is defined as "scattered areas of fibroglandular density," class C is defined as "heterogeneously dense," and class D is defined as "extremely dense." The two class CNN classifier 110 may be configured to classify an image into a high or low class to produce two probabilities ($P_{low}$, $P_{high}$) per image. The low class may include classes A and B, while the high class may include classes C and D. Both CNN classifiers may be trained on weakly labeled images from multiple imaging sites and multiple annotators. In some aspects, the probabilities ($P_A$, $P_B$, $P_C$, $P_D$ or $P_{low}$, $P_{high}$) sum to a value of 1, wherein the highest probability indicates the most likely class. To assign an overall breast tissue density class to an exam, the results of the two class and four class models are stored in features vector 36. The features vector is provided as input to a whole image boundary decision classifier 125, which may include any ensemble algorithm such as a random forest classifier, and the classifier 125 assigns a final breast tissue density (class A, class B, class C, or class D) label to the overall exam.

FIG. 4 shows a flow diagram for components of a four class classifier, according to the embodiments provided herein. In this embodiment, the two class CNN classifier and the four class CNN classifier are operated as described with respect to FIG. 3. An additional model, the patch model and risk classifier 115 is added to improve discernment between class X and class Y. The patch model and risk classifier 115 produces two probabilities ($P_{X2}$, $P_{Y2}$) per image, which corresponds to a likelihood of being classified into class X or class Y, wherein X and Y are classes along a boundary decision. If an image is classified as class Y, additional follow-up testing may be recommended. In this case, each image may be analyzed to provide eight probabilities per image, for a total of 32 features for the imaging set. In this example, the BIRADS 5$^{th}$ edition standard may be used, such that class X corresponds to class B and class Y corresponds to class C.

The patch model and risk classifier 115 increases the accuracy and improves performance/consistency between discerning between images with class X or class Y tissue density. In some aspects, the tissue image density classifier of FIG. 4 has improved accuracy over the tissue image density classifier of FIG. 3.

Figure 5:
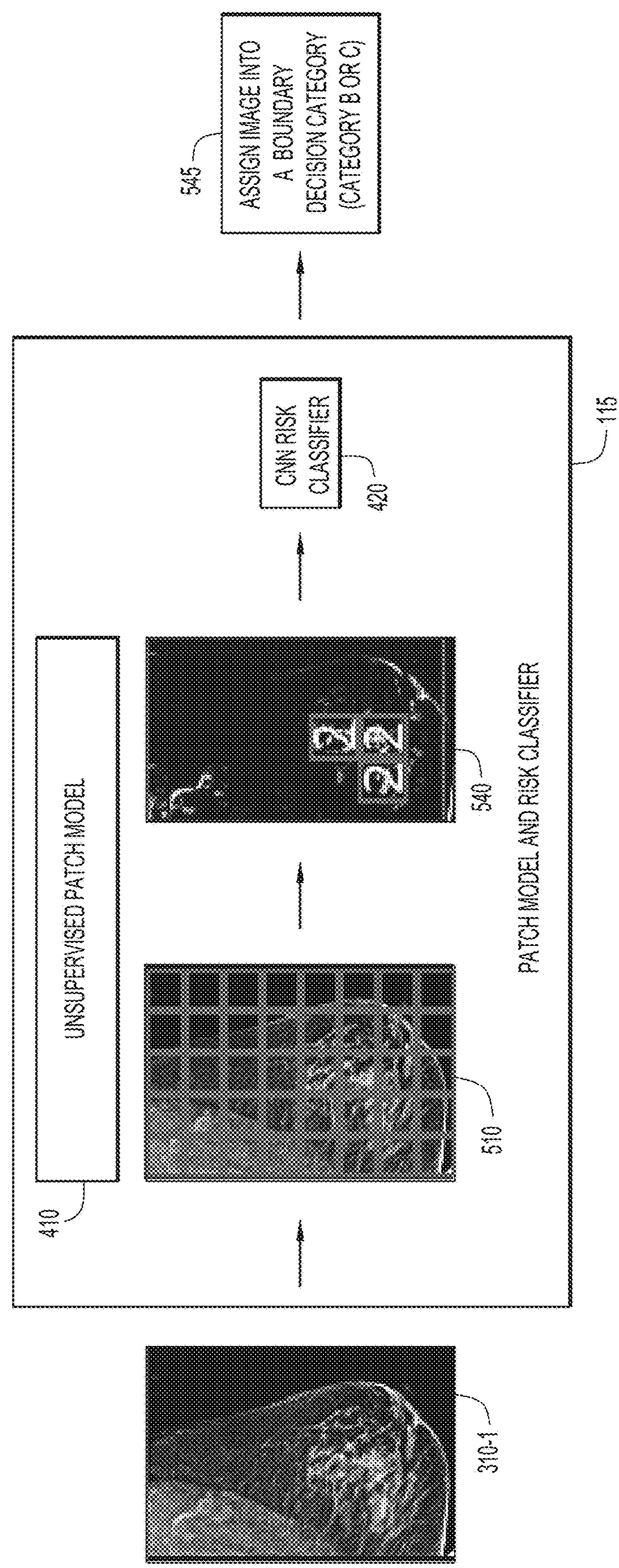
FIG. 5 is an illustration showing operations of the unsupervised patch model and convolutional neural network risk classifier based on FIG. 4, according to an embodiment of the present invention.

FIG. 5 shows a flow diagram of the patch model and risk classifier 115. The patch model and risk classifier may include two machine learning models, a machine learning model for the patch model 410 and another machine learning model for the risk classifier 420. In aspects, both machine learning models may be CNNs.

Each image (e.g., four mammography images) may be segmented into cells (by patch model 410) based upon a grid, dividing the image into cells with a size (e.g., 1 cm by 1 cm), as shown in image 510. Each cell is classified into a class by the patch model 410 (e.g., for three classes 0, 1, or 2; for two classes 0 or 1; etc.) according to the aggregate intensity in that cell (e.g., percentage of white pixels which corresponds to dense tissue) in the cell, as shown in classified cells 540. These labeled cells may be provided to risk classifier 420, for further analysis.

The labeled (e.g., 0, 1, 2) cells as shown in classified cells 540 are supplied to another CNN, risk classifier 420, to produce four image level classifications at 545. Based on the BIRAD 5$^{th}$ edition guidelines, the CNN risk classifier will classify the image into class B or class C.

Thus, CNN risk classifier receives as input a matrix of cell density values (e.g., 0, 1, 2) and produces a (B, C) classification, for the whole original image. This set of (B, C) probabilities ($P_{B2}$, $P_{C2}$) may be added to the other probabilities (from the four class and two class classifiers) of the features vector, for input to the whole image boundary decision classifier 125 (e.g., a type of ensemble classifier, such as a random forest classifier) that produces a breast density classification (A, B, C, or D) at output 490 for the entire image as shown in FIG. 4. In some aspects, the output is a tissue density score reflecting a probability that the images belong to a particular BIRADS $5^{th}$ edition class.

In some aspects, ordering of the classes matters. For the four class classifier, a modified loss function is utilized that adds a penalty for non-adjacent misclassification errors, with the maximum penalty given to W/Z classification errors. The loss function penalizes large classification errors (e.g., misclassifying a class W image as a non-adjacent class Y or Z image) more than small classification errors (e.g., misclassifying a class W image as an adjacent class X image). The two class classifiers may use binary cross-entropy as a loss function.

For the patch model, analysis is performed in an unsupervised manner, wherein boundaries are not provided on the image (only text or other annotation indicating whether lesions or cancerous masses are present). By dividing the image into cells, and training the system to label each cell, characteristics of strong labeling are mimicked, allowing the output of the patch model and risk classifier 115 to improve classification of the whole image boundary decision classifier 125.

Figure 6:
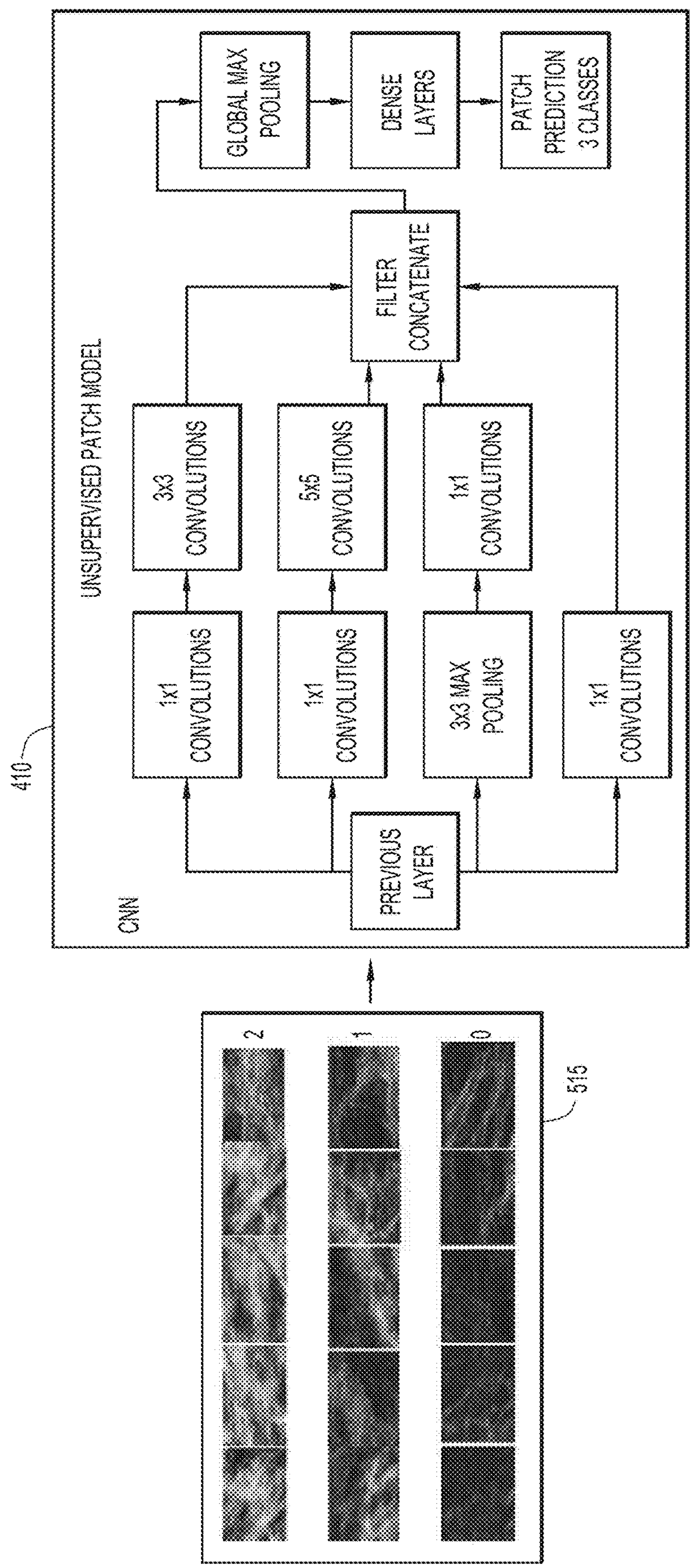
FIG. 6 is an illustration showing additional details of an example unsupervised patch model of FIG. 5, according to an embodiment of the present invention.

FIG. 6 shows an illustration of an example configuration of the patch model 410, and in particular, additional details regarding an example CNN used in patch model 410. This illustration details convolution and pooling operations as well as concatenation of data, which pertain to a single layer of the CNN. The patch model CNN may comprise a plurality of such layers, e.g., up to 300 layers or more.

To train the patch model 410, unsupervised clustering (k-means) may be applied to form clusters of training images from classes X and Y, or based on the BIRADS $5^{th}$ edition, classes B and C. The system may cluster the set of images into any number of suitable groups for further analysis. In some aspects, the value of k may be set to 2 or 3. In other aspects, k may be set to a higher value and the clusters later combined.

The resulting binary images may be divided into cells with squares of size 1 cm by 1 cm, and each cell may be labeled 0, 1, or 2 according to the percentage of white in the cell, wherein white corresponds to an amount of dense tissue cluster in the cell. The patch model CNN may be trained to classify cells (patches) into an intensity category (e.g., 0, 1, 2) using this automatically labeled training data.

To then solve the (B, C) classification problem, another CNN (risk classifier 420) that takes as input a matrix of (0, 1, 2) cell density values from patch model 410 and produces a (B, C) classification for the whole original image is trained. Once trained, the patch model and risk classifier 115 may accept unlabeled images and generate as output, a B/C classification in an automated manner, as shown in FIG. 5.

Figure 7:
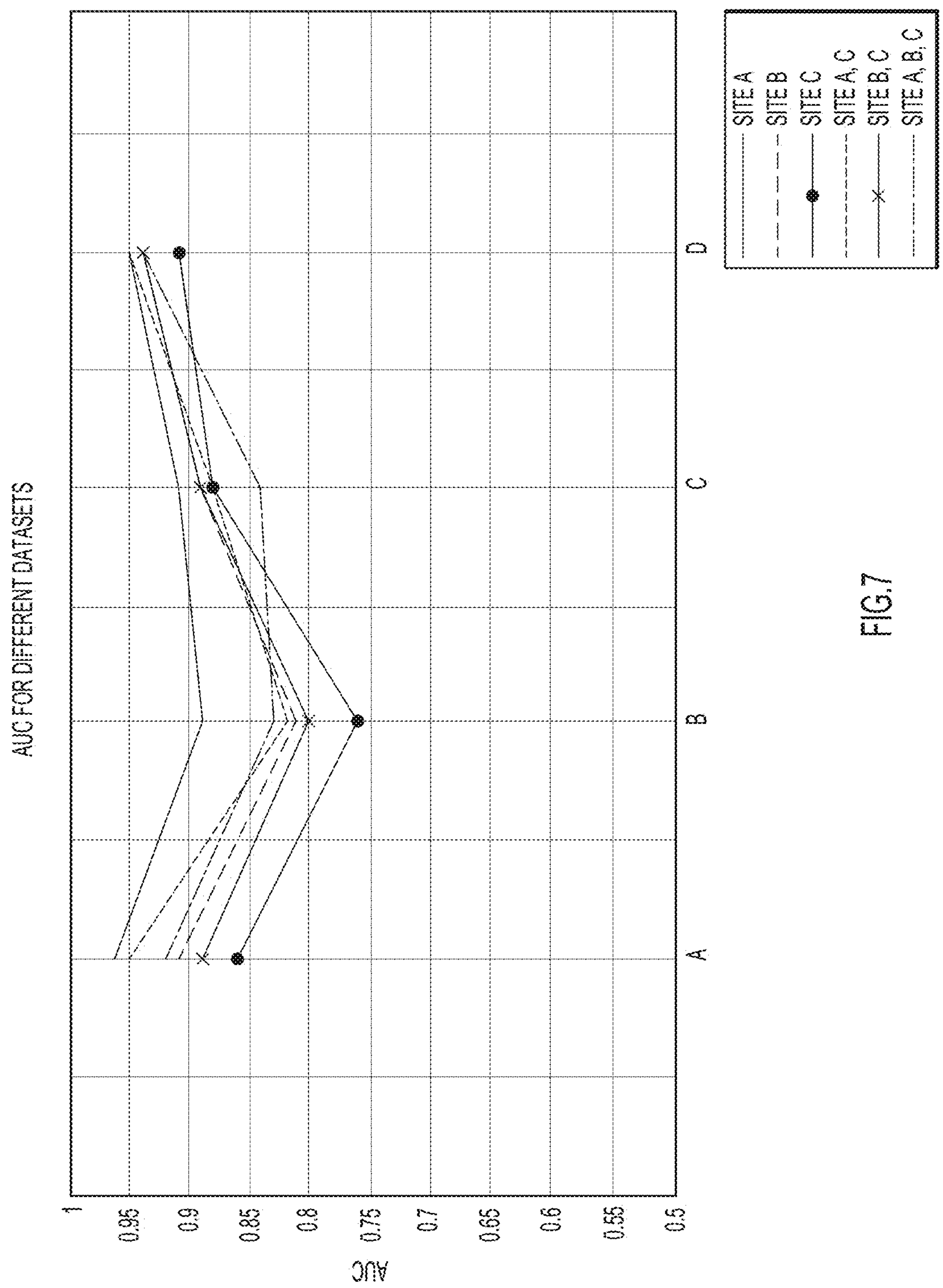
FIG. 7 is a graph showing the AUC for each BIRADS class based on the $5^{th}$ edition guidelines, wherein training may be performed using mixed data annotated by BIRADS $4^{th}$ or $5^{th}$ guidelines, according to an embodiment of the present invention.
Figure 8:
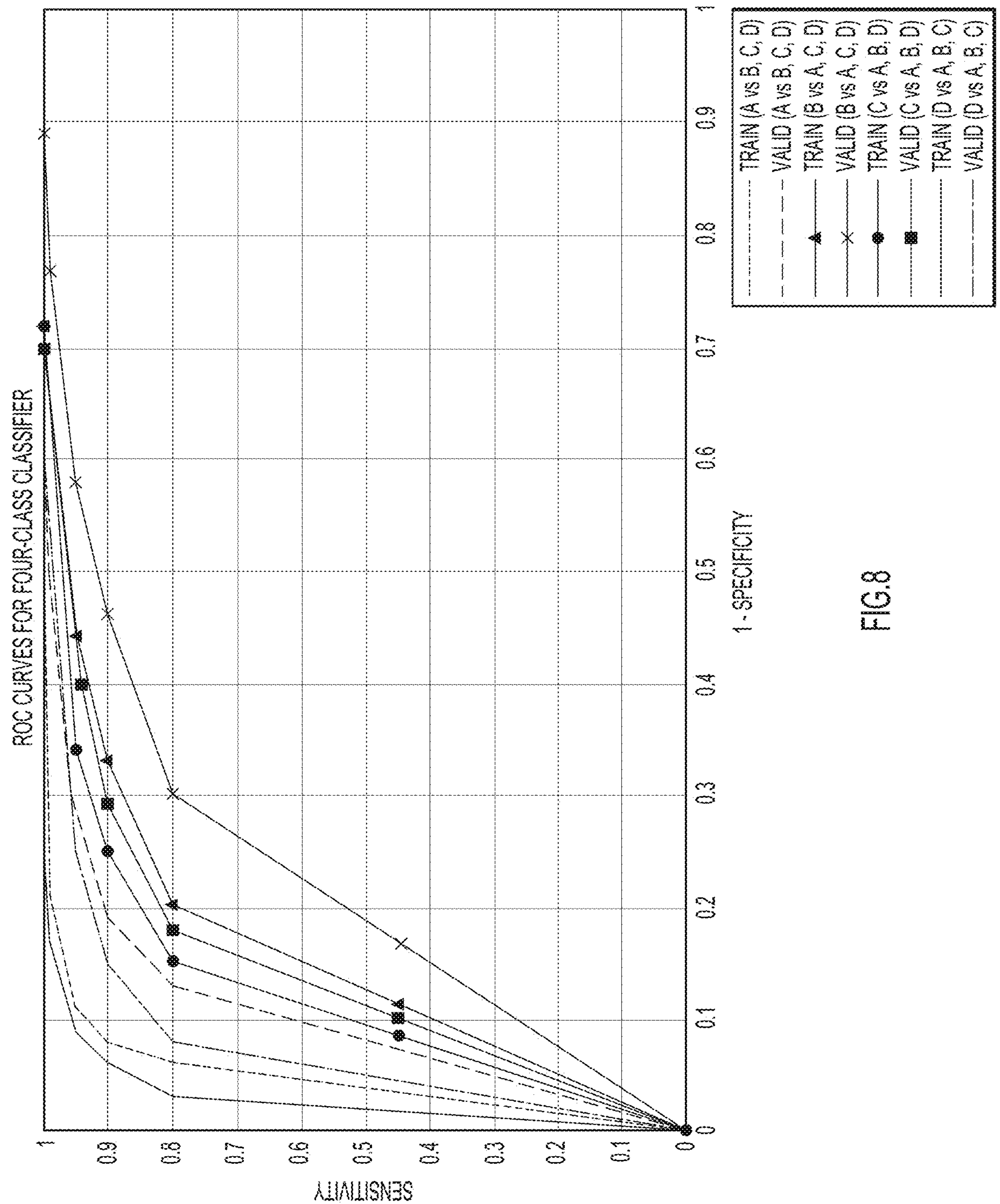
FIG. 8 is a graph showing results for the four class classifier, according to an embodiment of the present invention.

FIGS. 7 and 8 refer to experimental data, and are described below in the results section.

Figure 9:
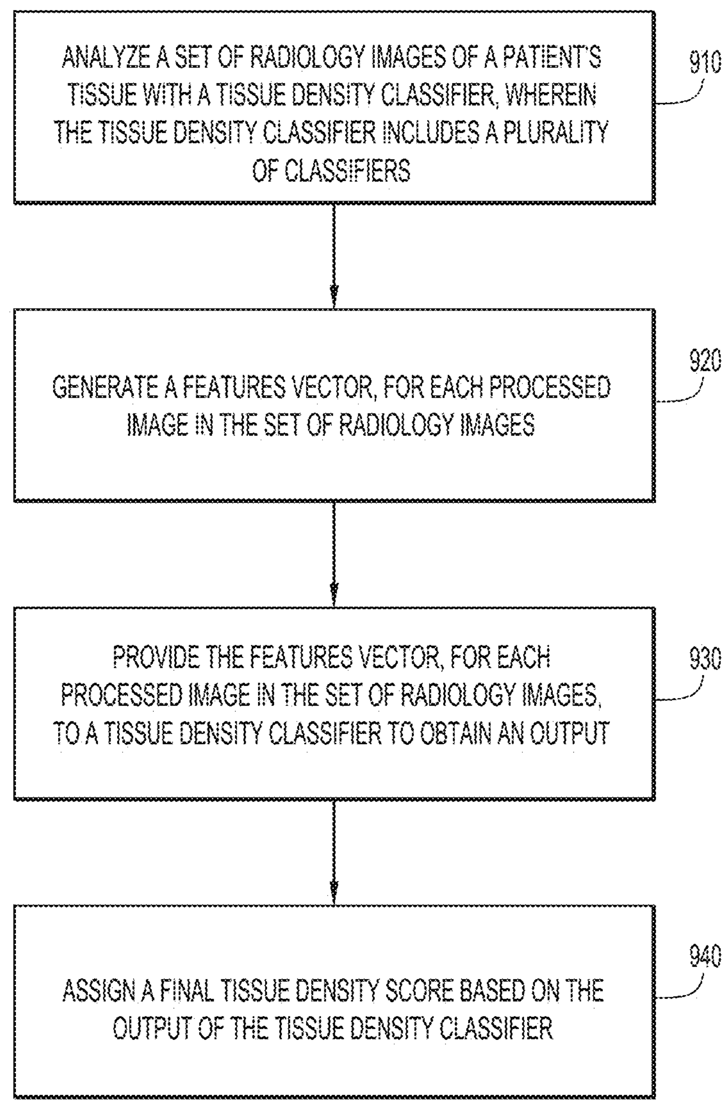
FIG. 9 is a high level flowchart of example operations for the tissue density image classifier, according to an embodiment of the present invention.

FIG. 9 shows a high level flow diagram of example operations according to the embodiments provided herein. At operation 910, a set of images of a patient's tissue is analyzed with a tissue density classifier, wherein the tissue density classifier includes a plurality of classifiers. At operation 920, a features vector is generated, for each processed image in the set of radiology images, based on the processing. At operation 930, the features vector is provided, for each processed image in the set of radiology images, to a tissue density classifier to obtain an output. At operation 940, a final tissue density score is assigned based on the output of the tissue density classifier.

Present techniques provide automated identification of at-risk patients using machine learning techniques. This approach provides an improvement in a technological field, as the combination of algorithms results in more accurate and reproducible classification. Further, these techniques may be used to train a classification system to achieve accurate results despite training data with mixed standards and/or inconsistent annotations by different physicians at different sites. Further, the unsupervised patch model and the CNN risk model emulates strong labeling, allowing this approach to be used with weakly labeled data sets, to improve training and thereby classification at the decision boundary between B and C classes.

Present techniques automate patient image classification in an automated, reproducible and accurate manner, to identify patients that may need additional screening due to the presence of high density tissue. This analysis may help identify at-risk patients to provide early intervention, instead of delaying treatment until the lesion or mass is large enough to be distinguished from high density pathology. This approach is integrated into a practical application, relying on multiple machine learning techniques to analyze digitized data and provide notifications as needed. In some aspects, a controller may be present which initiates analysis by the patch model and risk classifier of FIG. 4, if the four class CNN classifier and the two class CNN classifier of FIG. 3 classify the image as high density tissue. In other aspects, the controller may automatically perform additional screening when additional imaging data may be obtained by the same instrument (e.g., does not require a change in modality such as from a CT scanner to a MRI machine). In this case, the additional screening may be performed immediately after the initial screening (e.g., during the same appointment). In other aspects, the controller may automatically schedule follow-up testing.

It will be appreciated that the embodiments described above and illustrated in the drawings represent only a few of the many ways of implementing embodiments for automating analysis of tissue density, or any imaging process in which boundary identification is not provided (e.g., weak labeling) within the image.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing system employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, tissue density image classifier 15, etc.). These systems may include any type of monitors and input devices (e.g., keyboard, mouse, voice recognition, etc.) to enter and/or view information.

It is to be understood that the software (e.g., a tissue density image classifier 15 comprising a four class CNN classifier 105, a two class CNN classifier 110, a patch model and risk classifier 115, a features vector assembler 120, an whole image boundary decision classifier 125, and a flagging and alerts engine 130, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., a tissue density image classifier 15 comprising a four class CNN classifier 105, a two class CNN classifier 110, a patch model and risk classifier 115, a features vector assembler 120, an image boundary decision classifier 125, and a flagging and alerts engine 130, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., imaging data 32, training data 34, features vectors 36, image classification data 38, etc.). The database system may be implemented by any number of any conventional or other databases, data stores or storage structures (e.g., files, databases, data structures, data or other repositories, etc.) to store information (e.g., imaging data 32, training data 34, features vectors 36, image classification data 38, etc.). The database system may be included within or coupled to the server and/or client systems. The database systems and/or storage structures may be remote from or local to the computer or other processing systems, and may store any desired data (e.g., imaging data 32, training data 34, features vectors 36, image classification data 38, etc.).

The present invention embodiments may employ any number of any type of user interface (e.g., Graphical User Interface (GUI), command-line, prompt, etc.) for obtaining or providing information (e.g., imaging data 32, training data 34, features vectors 36, image classification data 38, etc.), where the interface may include any information arranged in any fashion. The interface may include any number of any types of input or actuation mechanisms (e.g., buttons, icons, fields, boxes, links, etc.) disposed at any location to enter/display information and initiate desired actions via any suitable input devices (e.g., mouse, keyboard, etc.). The interface screens may include any suitable actuators (e.g., links, tabs, etc.) to navigate between the screens in any fashion.

The output of the tissue density image classifier 15 may include any information arranged in any fashion, and may be configurable based on rules or other criteria to provide desired information to a user (e.g., classification results, risk classes, recommendations for follow-up testing, etc.).

The present invention embodiments are not limited to the specific tasks or algorithms described above, but may be utilized for any application involving analysis of medical images. Further, while the present examples are in the context of deep learning algorithms (e.g., such as CNN), any suitable classification algorithm may be used. Further, this approach may be generally applicable to analyze images in which strong labeling is not available, and is not limited to medical implementations. Further, any pre-determined, standard, or custom classifications may be used with the techniques provided herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

EXAMPLES

Example 1

The models were trained and tested on thousands of images from different sites with multiple annotators, and different annotation standards, including a mix of BIRADS $4^{th}$ and $5^{th}$ edition standards. Performance was evaluated by ROC analysis and kappa statistics. The models were shown to achieve high AUC despite the mixed standards inconsistent annotations.

The data was collected from three sites and analyzed according to classes provided in BIRADS 4th and 5th editions. The proposed algorithms were validated on data acquired from three hospitals, referred to as Site A, Site B or Site C. The breast density assessments in the reports associated with each exam provided the ground truth. The majority of the data in this preliminary study was acquired on Hologic devices, along with some Siemens images from Site C. Site A provided the largest amount of data, with around 70% of the images annotated using the $4^{th}$ BIRADS standard. Sites B and C had a greater percentage of BIRADS 5 data.

A detailed breakdown of the training and validation data is provided in Table 1. Table 2 shows the vendor and BIRADS standard distribution of the Site C data.

TABLE 1

Data description

| Site | Total No of images | No of BIRADS 4 | No of BIRADS 5 |
|---|---|---|---|
| A | 26760 | 18732 | 8028 |
| B | 6832 | 1504 | 5328 |
| C | 6364 | 2928 | 3464 |
| Total | 39956 | 23164 | 16820 |

Multiple ROC analyses were performed on the first version of the algorithm that combines the two and four class classifiers to produce a study-level breast tissue density assessment. A plot of the AUC for each BIRADS class is shown in 6. Each line in the plot represents the results of the models trained and tested on different combinations of site data. For example, the line labeled purple was trained with 60% of the Site B and Site C data, and tested on the remaining 40%.

TABLE 2

Vendor and BIRADS standard distribution for Site C

| Site C | No of BIRADS 4 | No of BIRADS 5 |
|---|---|---|
| Hologic | 0 | 1620 |
| Siemens | 2872 | 1872 |

As shown in FIG. 7, and based on BIRADS $5^{th}$ edition guidelines, the classification accuracy of classes A and D was generally higher than B and C for all combinations, due to the difference between B and C being more subjective and more affected by the transition from BIRADS 4 to 5. The Site C model performed the worst because Site C had an even mix of BIRADS 4 and 5 and was the only site that included data from a different vendor. The performance of classes B and C was the best for Site A, which had the most data.

Finally, ROC curves were generated for the binary one-vs-all decisions for each BIRADS class using the four class image-level classifier. FIG. 8 shows training and validation ROC curves for each class with combined data from all three sites. As before, the performance for classes A and D exceeded the performance for classes B and C.

The classifier's agreement with the ground truth and kappa statistics for the training, validation, and test set were calculated, as shown in Table 3. Note that kappa values in this range were considered to represent moderate agreement, which was an improvement given the mixed annotation standards present in the datasets. The typical physician's agreement with himself/herself when reading the same exam multiple times may range from 62-85%, with inter-rater agreement ranging from 68-74%, as reported in literature.

TABLE 3

Per-class agreement and kappa statistics

| | A | B | C | D |
|---|---|---|---|---|
| Train/Valid | | | | |
| Accuracy (Agreement) | 0.8697 | 0.6151 | 0.7168 | 0.9283 |
| Kappa value | | 0.5512 | | |
| Test | | | | |
| Accuracy (Agreement) | 0.8767 | 0.6009 | 0.6628 | 0.7556 |
| Kappa value | | 0.53 | | |

What is claimed is:

1. A method for processing digitized radiology images to perform a tissue density assessment, the method comprising:

analyzing a set of radiology images of a patient's tissue with a tissue density classifier comprising a first machine learning classifier and a second machine learning classifier, wherein the first machine learning classifier is trained with first training images to produce a plurality of first probabilities for each radiology image indicating a likelihood of that image belonging to at least four different corresponding tissue density classes each associated with an amount of high density tissue present in that image, wherein the second machine learning classifier is trained with second training images to produce second probabilities for each radiology image indicating a likelihood of that image belonging to at least two different corresponding second classes, wherein the at least two different corresponding second classes include a high tissue density class and a low tissue density class, wherein the high tissue density class includes at least two of the tissue density classes of the first machine learning classifier with a high amount of high density tissue requiring additional screening and the low tissue density class includes at least two of the tissue density classes of the first machine learning classifier with a low amount of high density tissue not requiring additional screening, and wherein each second class includes at least two of the tissue density classes of the first machine learning classifier that are non-overlapping with the tissue density classes of each other second class;

generating a features vector, for each processed image in the set of radiology images, wherein the features vector for each processed image includes the first and second probabilities for that processed image produced by the first and second machine learning classifiers;

determining a final tissue density classification for the patient's tissue from among the tissue density classes of the first machine learning classifier by a decision classifier based on the features vector for each processed image in the set of radiology images; and providing, by the tissue density classifier, the final tissue density classification for the patient's tissue and a corresponding recommendation for the additional screening at a modality.

2. The method of claim 1, wherein analyzing the set of radiology images with the tissue density classifier comprises analyzing the set with an unsupervised patch model classifier and a risk classifier, wherein results of the risk classifier for each processed image are added to the features vector for that image.

3. The method of claim 2, wherein the unsupervised patch model classifier segments each image of the set of images into a plurality of cells and labels each cell based on an intensity of pixels in the cell.

4. The method of claim 3, wherein an output of the unsupervised patch model classifier is provided to the risk classifier that determines a likelihood of classification into a class corresponding with a reduced risk of hidden cancerous masses and a likelihood of classification into a different class corresponding with an increased risk of hidden cancerous masses due to a presence of high density tissue.

5. The method of claim 1, wherein the tissue density classifier further comprises a third machine learning classifier trained with third training images to produce third probabilities for each radiology image indicating a likelihood of that image belonging to at least two different corresponding third classes, wherein the at least two different corresponding third classes include a first tissue density class of the first machine learning classifier with a high amount of high density tissue requiring additional screening and a second adjacent tissue density class of the first machine learning classifier with a low amount of high density tissue not requiring additional screening, and wherein the features vector for each processed image further includes the third probabilities for that processed image produced by the third machine learning classifier.

6. The method of claim 1, wherein the first machine learning classifier includes four tissue density classes that are ordered based on increasing amounts of dense tissue.

7. The method of claim 1, wherein the high tissue density class comprises a first combination of two adjacent ordered tissue density classes of the first machine learning classifier, and wherein the low tissue density class comprises a second combination of two adjacent ordered tissue density classes of the first machine learning classifier.

8. The method of claim 2, wherein the unsupervised patch model classifier and the risk classifier each comprises at least one convolutional neural network (CNN).

9. The method of claim 2, wherein analyzing the set of radiology images with the tissue density classifier further comprises analyzing the set with:

the first machine learning model classifier with four tissue density classes, wherein the four tissue density classes are ordered and a loss function is used to penalize non-adjacent classification errors; and the second machine learning classifier with two classes, wherein an entropy function is used to penalize classification errors.

10. A system for processing digitized radiology images to perform a tissue density assessment comprising:

one or more computer processors;

one or more computer readable storage media;

program instructions stored on the one or more computer readable storage media for execution by at least one of the one or more computer processors, the program instructions comprising instructions to:

analyze a set of radiology images of a patient's tissue with a tissue density classifier comprising a first machine learning classifier and a second machine learning classifier, wherein the first machine learning classifier is trained with first training images to produce a plurality of first probabilities for each radiology image indicating a likelihood of that image belonging to at least four different corresponding tissue density classes each associated with an amount of high density tissue present in that image, wherein the second machine learning classifier is trained with second training images to produce second probabilities for each radiology image indicating a likelihood of that image belonging to at least two different corresponding second classes, wherein the at least two different corresponding second classes include a high tissue density class and a low tissue density class, wherein the high tissue density class includes at least two of the tissue density classes of the first machine learning classifier with a high amount of high density tissue requiring additional screening and the low tissue density class includes at least two of the tissue density classes of the first machine learning classifier with a low amount of high density tissue not requiring additional screening, and wherein each second class includes at least two of the tissue density classes of the first machine learning classifier that are non-overlapping with the tissue density classes of each other second class;

generate a features vector, for each processed image in the set of radiology images, wherein the features vector for each processed image includes the first and second probabilities for that processed image produced by the first and second machine learning classifiers;

determine a final tissue density classification for the patient's tissue from among the tissue density classes of the first machine learning classifier by a decision classifier based on the features vector for each processed image in the set of radiology images; and provide, by the tissue density classifier, the final tissue density classification for the patient's tissue and a corresponding recommendation for the additional screening at a modality.

11. The system of claim 10, wherein the system further comprises an unsupervised patch model classifier and a risk classifier, wherein the program instructions further comprise instructions to analyze the set of radiology images with the unsupervised patch model classifier and the risk classifier, and wherein results of the risk classifier for each processed image are added to the features vector for that image.

12. The system of claim 11, wherein the program instructions further comprise instructions to segment each image of the set of images into a plurality of cells and to label each cell based on an intensity of pixels in the cell.

13. The system of claim 12, wherein the program instructions further comprise instructions to:

provide an output of the unsupervised patch model classifier to the risk classifier to determine a likelihood of classification into a class corresponding with a reduced risk of hidden cancerous masses and a likelihood of classification into a different class corresponding with an increased risk of hidden cancerous masses due to a presence of high density tissue.

14. The system of claim 10, wherein the tissue density classifier further comprises a third machine learning classifier trained with third training images to produce third probabilities for each radiology image indicating a likelihood of that image belonging to at least two different corresponding third classes, wherein the at least two different corresponding third classes include a first tissue density class of the first machine learning classifier with a high amount of high density tissue requiring additional screening and a second adjacent tissue density class of the first machine learning classifier with a low amount of high density tissue not requiring additional screening, and wherein the features vector for each processed image further includes the third probabilities for that processed image produced by the third machine learning classifier.

15. The system of claim 10, wherein the first machine learning classifier includes four tissue density classes, and the program instructions further comprise instructions to order the four tissue density classes based on increasing amounts of dense tissue.

16. The system of claim 10, wherein the high tissue density class comprises a first combination of two adjacent ordered tissue density classes of the first machine learning classifier, and wherein the low tissue density class comprises a second combination of two adjacent ordered tissue density classes of the first machine learning classifier.

17. The system of claim 11, wherein the unsupervised patch model classifier and the risk classifier each comprises at least one convolutional neural network (CNN).

18. The system of claim 11, wherein the program instructions further comprise instructions to:

analyze the set of radiology images with the first machine learning classifier with four tissue density classes, wherein the four tissue density classes are ordered and a loss function is used to penalize non-adjacent classification errors; and analyze the set of radiology images with the second machine learning classifier with two classes, wherein an entropy function is used to penalize classification errors.

19. A computer program product for processing digitized radiology images to perform a tissue density assessment, the computer program product comprising one or more computer readable storage media collectively having program instructions embodied therewith, the program instructions executable by a computer to cause the computer to:

analyze a set of radiology images of a patient's tissue with a tissue density classifier comprising a first machine learning classifier and a second machine learning classifier, wherein the first machine learning classifier is trained with first training images to produce a plurality of first probabilities for each radiology image indicating a likelihood of that image belonging to at least four different corresponding tissue density classes each associated with an amount of high density tissue present in that image, wherein the second machine learning classifier is trained with second training images to produce second probabilities for each radiology image indicating a likelihood of that image belonging to at least two different corresponding second classes, wherein the at least two different corresponding second classes include a high tissue density class and a low tissue density class, wherein the high tissue density class includes at least two of the tissue density classes of the first machine learning classifier with a high amount of high density tissue requiring additional screening and the low tissue density class includes at least two of the tissue density classes of the first machine learning classifier with a low amount of high density tissue not requiring additional screening, and wherein each second class includes at least two of the tissue density classes of the first machine learning classifier that are non-overlapping with the tissue density classes of each other second class;

generate a features vector, for each processed image in the set of radiology images, wherein the features vector for each processed image includes the first and second probabilities for that processed image produced by the first and second machine learning classifiers;

determine a final tissue density classification for the patient's tissue from among the tissue density classes of the first machine learning classifier by a decision classifier based on the features vector for each processed image in the set of radiology images; and provide, by the tissue density classifier, the final tissue density classification for the patient's tissue and a corresponding recommendation for the additional screening at a modality.

20. The computer program product of claim 19, wherein the program instructions further cause the computer to:

analyze the set of radiology images with an unsupervised patch model classifier that generates an output comprising classification of cells of an image based on an intensity of pixels in the cells; and provide the output of the unsupervised patch model classifier to a risk classifier to determine a likelihood of classification into a class corresponding with a reduced risk of hidden cancerous masses and a likelihood of classification into a different class corresponding with an increased risk of hidden cancerous masses due to a presence of high density tissue, wherein results of the risk classifier for each processed image are added to the features vector for that image.

* * * * *